United States Patent [19]
Schiweck

[11] 3,940,481
[45] Feb. 24, 1976

[54] TREATMENT OF HEPATIC COMA WITH ISOMALTITOL

[75] Inventor: Hubert Schiweck, Obrigheim, Germany

[73] Assignee: Suddeutsche Zucker-Aktiengesellschaft, Mannheim, Germany

[22] Filed: Feb. 12, 1974

[21] Appl. No.: 441,888

[30] Foreign Application Priority Data
Feb. 14, 1973  Germany............................ 2307251

[52] U.S. Cl. ............................................... 424/180
[51] Int. Cl.² ........................................ A61K 31/70
[58] Field of Search ........... 426/190, 213, 217, 380; 424/180

[56] References Cited
UNITED STATES PATENTS
3,705,039  12/1972  Mitsuhashi...................... 426/190 X FOREIGN PATENTS OR APPLICATIONS
2,217,628  10/1973  Germany ........................... 424/180

OTHER PUBLICATIONS
Wolfrom, J. Am. Chem. Soc. Vol. 74, Feb. 20, 1952 pp. 1062–1064.

Primary Examiner—Stanley J. Friedman
Assistant Examiner—A. P. Fagelson
Attorney, Agent, or Firm—Armstrong, Nikaido & Wegner

[57] ABSTRACT

Isomaltitol has also been discovered to be valuable as a therapeutic agent for chronic obstipation and liver injury, in particular for the treatment and prophylaxis of hepatopathy, dyspepsia, dysbiosis and disturbances in the nourishment of infants, and their consequent phenomena.

3 Claims, No Drawings

TREATMENT OF HEPATIC COMA WITH ISOMALTITOL

Hepatopathia, specifically chronic hepatopathia, and in particular hepatic encephalopathy, are diseases which hitherto it has proved possible to deal with only to an unsatisfactory degree by medicinal therapy. The known medicaments prove ineffective in many cases and in addition it was found that the use thereof sometimes involved risk due to their considerable toxicity. It has also already been found that lactulose has an advantageous effect in such diseases but exhibits undesirable subsidiary effects inasmuch as it is available only in the form of a syrup mixture having a maximum of 70% lactulose, since it is itself difficult to crystallise. It has also already been proposed to employ raffinose for the purpose mentioned, but this is difficult to produce and excessively costly for practical employment.

These disadvantages are obviated on employing the therapeutic medium according to the invention. The medium is characterised by an isomaltitol content.

The medicament according to the invention possesses marked pharmacological efficacy. This efficacy consists of a healing and preventive effect in the case of hepatopathy, especially chronic hepatopathy and in particular hepatic encephalopathy, dyspepsia, dysbiosis, and also disturbances in the nourishment of infants, such as infant obstipation, pepsinogenous conditions in infants and the like, and the consequences thereof.

Since isomaltitol is, on passage through the small intestive, cracked and resorbed to a relatively insignificant extent, the main quantity passes into the large intentine. There, a portion of the isomaltitol is metabolised by the non-pathogenic bacteria, whereby bacteria growth and therewith intentine activity is encouraged. The consequence thereof is that the dry substance quantity excreted in the feces increases absolutely, as does also the bacteria content (albumin content) of the feces, as has been ascertained in feeding tests performed on rats.

EXAMPLE 1

Standard laboratory rats were allowed to feed on Altromin standard feed to the amount desired by the rat with the following results.

| Type of feed per day | Average quantity of excrement in g dry weight per day and animal | mg albumin mass in excrement per day and animal | Percentage of dry substance in the excrement |
|---|---|---|---|
| Altromin standard feed | 2.7 | 403 | 89 |
| Altromin standard feed + 2.5 g sugar + 2.5 g. isomaltite | 3.1 | 703 | 75 |
| Altromin standard feed + 5 g isomaltitol | 3.5 | 920 | 66 |

Due to the increased albumin synthesis, there is absorption of ammonium ions or amines from the intestine content and therewith detoxication thereof.

A further portion of the isomaltitol is broken down to organic acids, above all lactic acids, and this results in an observed reduction of the pH value in the final intestine. In turn, the reduction of the pH value results in hindrance of the activity of the flora responsible for the formation of toxic albumin decomposition products. These toxic albumin decomposition products, such as for example ammonia, phenol bodies and others, play an important part in the emergence of the diseases which can be prevented and combated by means of the medicament according to the invention.

The medicament according to the invention is especially suitable for oral or rectal delivery and can be prepared in any formulation suitable for the form of delivery selected in each particular instance. Application can be effected in pure form or together with conventional pharmaceutical carriers excipients. Suitable forms of delivery are for example powders, crystalline substances, instant powders, tablets, granules, lozenges, effervescent tablets, capsules, coated pills, syrup, paste, enemas (clysters) and the like. The medium can be combined with further therapeutically active agents, for example with antibiotics, sulphonamides and vitamins. Additionally, it is also possible to add flavour-correcting agents. They may also - with unchanged indication- be processed or contained in foodstuffs, in particular dietetic foodstuffs and foodstuffs for infants and children.

Since the medicament according to the invention is non-toxic when used in accordance with prescription in reasonable doses, the dosing employed may be almost optionally determined depending on specific requirements. Actually employed are daily doses between about 20 and 250 g, distributed throughout the day in small individual doses.

EXAMPLE 2.

Use of raffinose in clinical coma therapy

An elderly patient with chronic coma hepaticum due to alcoholic liver cirrhosis is given 150 grams isomaltitol daily per os. With a constant diet (40 grams protein daily), an initially good response is observed. The coma could be overcome in a way which is just as good as with neomycin therapy. Without the therapy, a relapse occurs which could, however, still be controlled again by isomaltitol. EEG-observations confirm the clinical course of the treatment.

This clinical investigation shows that isomaltitol possesses favorable activity in the case of porto-systemic encephalopathy.

EXAMPLE 3.

An elderly hospitalized patient with non-characteristic abdominal pains is given barium sulfate for 3 days. On the fourth day, an X-ray is taken of the empty abdomen from a rear posture, whereafter 20 grams isomalitol are administered. Thereafter, the same amounts of raffinose are administered every 30 minutes for a total period of 180 minutes. The calculation of the colonic volume from the X-rays gives a maximum volume increase of 400 ml.

EXAMPLE 4.

Reduction of the ammonia level in rats with a portocaval shunt

After application of a porto-caval shunt, rats show hyperammonaemia which, in the course of time, increases from a normal value of about 100µg./100 ml. to 600µg./100 ml.

For the treatment, 0.6 grams isomaltitol are administered to the animals three times daily for 48 hours by means of a stomach probe. The ammonia level is determined before and after the experiments. The ammonia level sinks markedly, in the case of the administration of isomaltitol.

EXAMPLE 5.

Rectal administration

A middleaged male patient with hepatic coma, stage III, is given a total of 1000 ml. of a 15% aqueous solution of isomaltitol, the pH of which is buffered, divided into three doses over the course of the day, administration at a rapid rate by means of a balloon catheter. After the treatment is carried out, there is observed an improvement of consciousness, an improvement of the EKG, and a reduction of the venous and arterial ammonia level. (Further treatment is by the oral administration of raffinose.)

EXAMPLE 6

Administration of isomalitol in doses of 20–150 grams daily, especially of 40–60 grams and advantageously of 46 grams, isomaltitol in 4 tablets (4 individual doses) are spread out over the day. A single dose corresponds to 11.5 grams isomaltitol.

What is claimed is:

1. Method for the treatment of hepatic coma, which method comprises administering enterally to the patient an amount of isomaltitol effective for treating said hepatic coma.
2. The method of claim 1 wherein the isomaltitol is applied at a dosage of about 20 to 250 grams per day.
3. The method of claim 2, wherein the dosage is about 100 grams per day.

* * * * *